US010463396B2

(12) United States Patent
Kleyman et al.

(10) Patent No.: US 10,463,396 B2
(45) Date of Patent: Nov. 5, 2019

(54) DEVICES FOR PERFORMING MINIMALLY INVASIVE SURGERY HAVING BELLOWS SUPPORT HOUSING

(71) Applicant: Conmed Corporation, Utica, NY (US)

(72) Inventors: Gennady Kleyman, Brooklyn, NY (US); Michael J. Augelli, Prospect, CT (US); Michael J. Kane, Clinton, CT (US); Mikiya Silver, New Haven, CT (US)

(73) Assignee: Conmed Corporation, Utica, NY (US)

( * ) Notice: Subject to any disclaimer, the term of this patent is extended or adjusted under 35 U.S.C. 154(b) by 226 days.

(21) Appl. No.: 15/790,658

(22) Filed: Oct. 23, 2017

(65) Prior Publication Data
US 2019/0117257 A1    Apr. 25, 2019

(51) Int. Cl.
*A61B 17/34* (2006.01)
*A61B 90/00* (2016.01)
*A61B 17/00* (2006.01)

(52) U.S. Cl.
CPC ...... *A61B 17/3462* (2013.01); *A61B 17/3423* (2013.01); *A61B 2017/00477* (2013.01); *A61B 2017/00862* (2013.01); *A61B 2017/3449* (2013.01); *A61B 2017/3464* (2013.01); *A61B 2017/3466* (2013.01); *A61B 2090/035* (2016.02)

(58) Field of Classification Search
CPC ............ A61B 17/3462; A61B 17/3423; A61B 2090/035
See application file for complete search history.

(56) References Cited

U.S. PATENT DOCUMENTS

| | | | |
|---|---|---|---|
| 4,844,484 A | 7/1989 | Antonini et al. | |
| 4,998,740 A | 3/1991 | Tellier | |
| 5,865,728 A * | 2/1999 | Moll ................. | A61B 17/0218 600/204 |
| 6,440,063 B1 * | 8/2002 | Beane ................. | A61B 42/10 600/207 |
| 6,482,181 B1 | 11/2002 | Racenet et al. | |
| 6,551,270 B1 | 4/2003 | Bimbo et al. | |

(Continued)

FOREIGN PATENT DOCUMENTS

KR    101022754 B1    3/2011

OTHER PUBLICATIONS

PCT International Search Report and Written Opinion dated Feb. 14, 2019, issued during the prosecution of PCT International Patent Application No. PCT/US2018/052527 (17 pages).

*Primary Examiner* — Christian A Sevilla
(74) *Attorney, Agent, or Firm* — Locke Lord LLP; Scott D. Wofsy

(57) ABSTRACT

An access device for surgical procedures includes a multi-port end cap having a rigid body with a flexible support sealingly mounted to the rigid body with a plurality of separate access ports for accommodating introduction of individual surgical instruments into a body of a patient. At least one of the access ports is sealingly attached to the flexible support and extends in a proximal direction therefrom. The flexible support is of a material more flexible than those of the rigid body and access ports to provide for relative angular movement of at least one of the access ports to provide flexibility for positioning surgical instruments introduced through the access ports. The flexible support can include at least one flexible bellow.

22 Claims, 16 Drawing Sheets

(56) References Cited

U.S. PATENT DOCUMENTS

| | | | |
|---|---|---|---|
| 6,595,946 B1 * | 7/2003 | Pasqualucci | A61B 17/3462 604/164.01 |
| 7,244,244 B2 | 7/2007 | Racenet et al. | |
| 7,753,901 B2 | 7/2010 | Piskun et al. | |
| 7,854,724 B2 | 12/2010 | Stearns et al. | |
| 7,892,337 B2 | 2/2011 | Palmerton et al. | |
| 7,930,782 B2 | 4/2011 | Chen | |
| 8,109,873 B2 | 2/2012 | Albrecht et al. | |
| 8,187,177 B2 | 5/2012 | Kahle et al. | |
| 8,187,178 B2 | 5/2012 | Bonadio et al. | |
| 8,226,553 B2 | 7/2012 | Shelton, IV et al. | |
| 8,251,900 B2 | 8/2012 | Ortiz et al. | |
| 8,262,622 B2 | 9/2012 | Gonzales et al. | |
| 8,273,017 B1 | 9/2012 | Moreno | |
| 8,328,761 B2 * | 12/2012 | Widenhouse | A61B 17/3462 604/164.08 |
| 8,475,490 B2 | 7/2013 | Hess et al. | |
| 8,480,683 B2 | 7/2013 | Fowler et al. | |
| 8,485,970 B2 | 7/2013 | Widenhouse et al. | |
| 8,574,153 B2 | 11/2013 | Richard | |
| 8,602,983 B2 | 12/2013 | Kleyman | |
| 8,763,895 B2 | 7/2014 | Colman et al. | |
| 8,764,647 B2 | 7/2014 | Kleyman | |
| 8,795,163 B2 | 8/2014 | Widenhouse et al. | |
| 8,795,223 B2 | 8/2014 | Stearns et al. | |
| 8,795,326 B2 | 8/2014 | Richard | |
| 8,945,002 B2 | 2/2015 | Oberlander et al. | |
| 9,101,354 B2 | 8/2015 | Albrecht et al. | |
| 9,113,951 B2 | 8/2015 | Richard et al. | |
| 9,131,835 B2 | 9/2015 | Widenhouse et al. | |
| 9,173,677 B2 | 11/2015 | Marczyk et al. | |
| 9,289,200 B2 | 3/2016 | Dang et al. | |
| 9,408,597 B2 | 8/2016 | Bonadio et al. | |
| 9,474,518 B2 | 10/2016 | Richard | |
| 9,597,112 B2 | 3/2017 | Stearns et al. | |
| 2005/0090717 A1 * | 4/2005 | Bonadio | A61B 17/0293 600/208 |
| 2009/0036745 A1 | 2/2009 | Bonadio et al. | |
| 2009/0227843 A1 | 9/2009 | Smith et al. | |
| 2010/0081880 A1 | 4/2010 | Widenhouse et al. | |
| 2011/0124967 A1 | 5/2011 | Morgan et al. | |
| 2011/0144437 A1 * | 6/2011 | Ortiz | A61B 17/3421 600/201 |
| 2013/0012782 A1 | 1/2013 | Stearns et al. | |
| 2016/0287817 A1 | 10/2016 | Mastri et al. | |
| 2017/0056064 A1 | 3/2017 | Zergiebel et al. | |

* cited by examiner

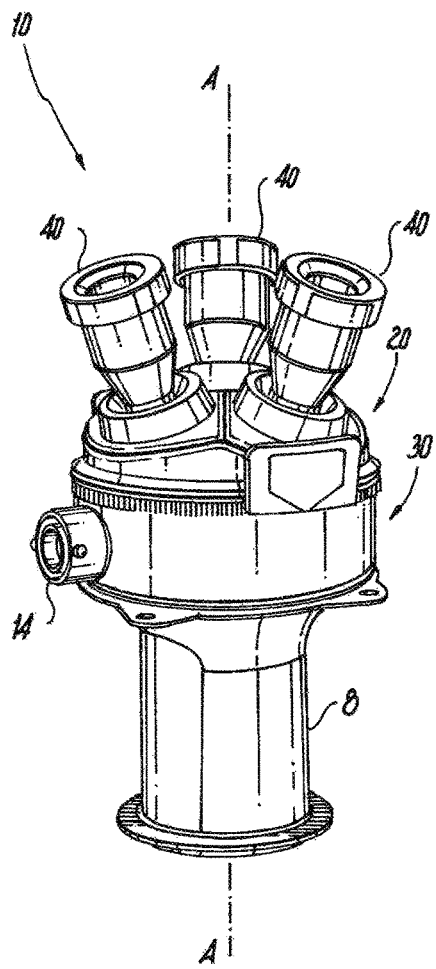
Fig. 1
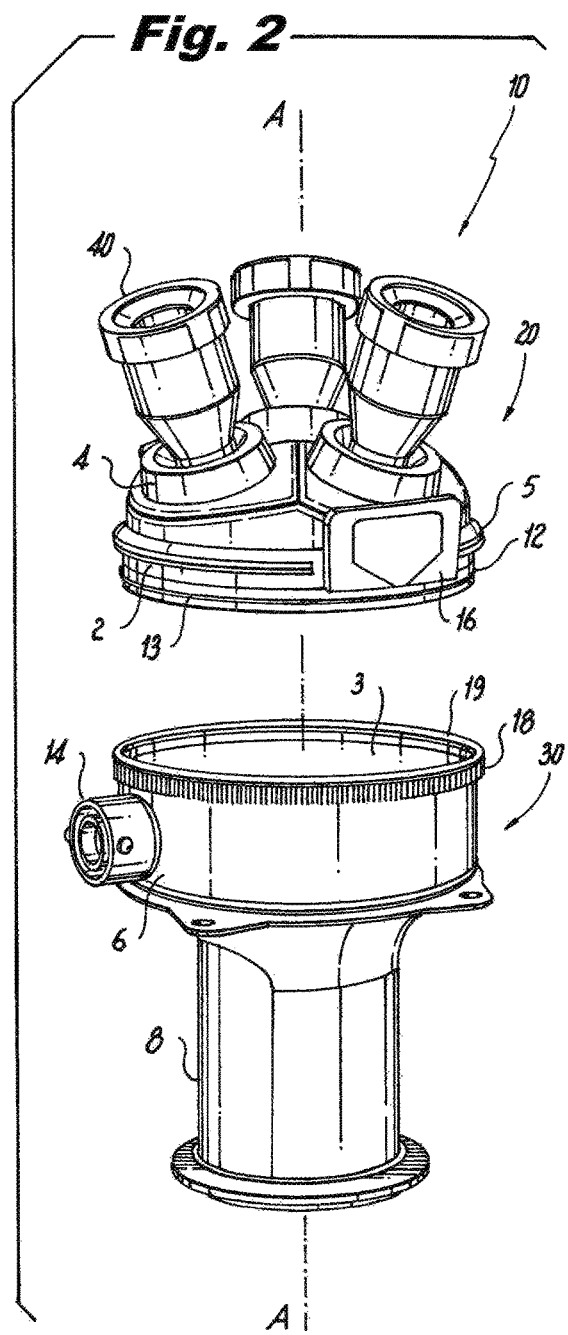

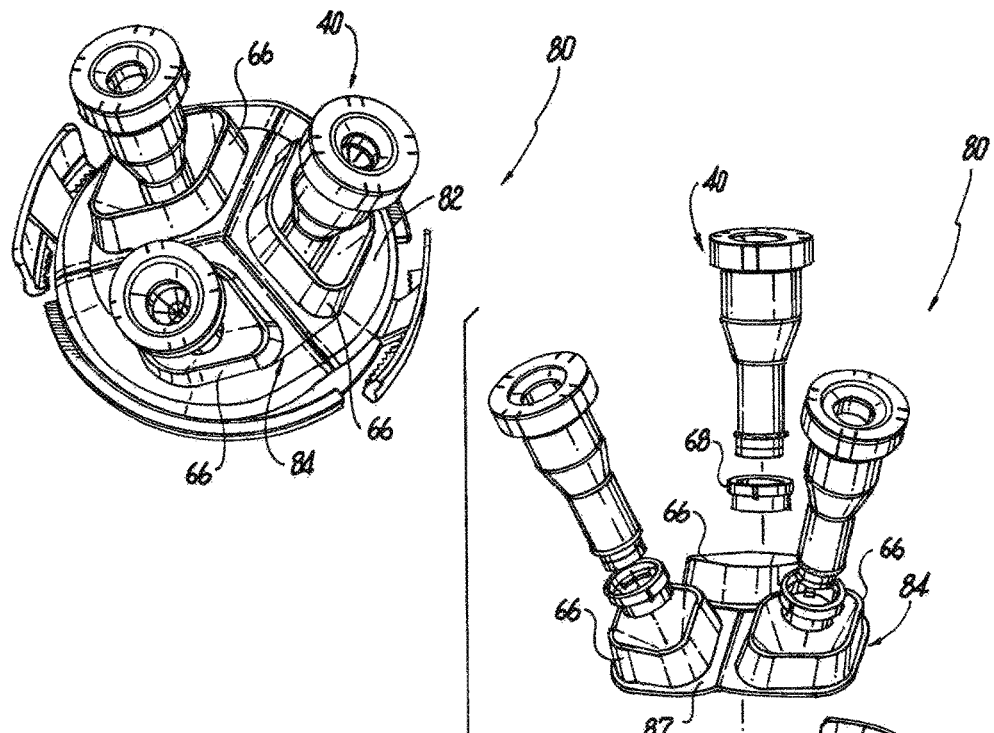
Fig. 19
Fig. 20
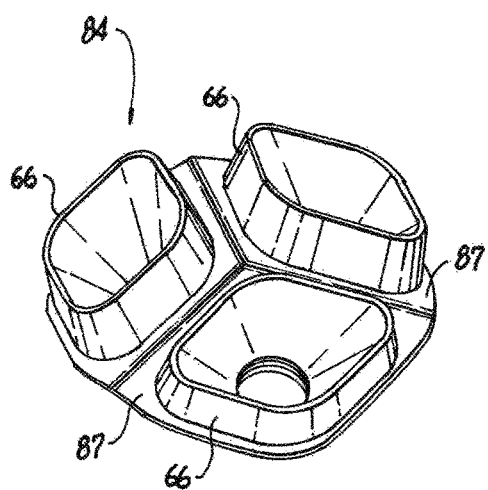
Fig. 21

DEVICES FOR PERFORMING MINIMALLY INVASIVE SURGERY HAVING BELLOWS SUPPORT HOUSING

BACKGROUND OF THE INVENTION

1. Field of the Invention

The subject invention is directed to surgical access devices, and more particularly, to multi-port access devices for minimally invasive surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures commonly involve filling or "insufflating" the abdominal (peritoneal) cavity with a pressurized fluid, such as carbon dioxide, to create what is referred to as a pneumoperitoneum.

The insufflation can be carried out by a surgical access device equipped to deliver insufflation fluid, or by a separate insufflation device, such as an insufflation (veress) needle. CONMED Corporation of Utica, N.Y., USA has developed unique surgical access devices that permit ready access to an insufflated surgical cavity without the need for conventional mechanical seals, and it has developed related gas delivery systems for providing sufficient pressure and flow rates to such access devices, as described in whole or in part in U.S. Pat. Nos. 7,854,724 and 8,795,223, the disclosures of which are both herein incorporated by reference in their entireties.

During typical laparoscopic procedures, a surgeon makes three to four small incisions, usually no larger than about twelve millimeters each. Typically the surgical access device is inserted into an incision using a separate inserter or obturator placed therein. Following insertion, the inserter is removed, and the trocar allows access for instruments to be inserted into the abdominal cavity.

A variety of larger access devices are also known in the art for accessing a surgical site through a single relatively large incision to perform minimally invasive procedures, rather than through multiple small incisions. Examples of such devices are disclosed in U.S. Patent Application Publication No. 2013/0012782, the disclosure of which is herein incorporated by reference in its entirety.

Trans-anal minimally invasive surgery (TAMIS) is a specialized minimally invasive approach to removing benign polyps and some cancerous tumors within the rectum and lower sigmoid colon. The benefit of TAMIS is that it is considered an organ-sparing procedure, and is performed entirely through the body's natural opening, requiring no skin incisions to gain access to a polyp or tumor. This scar-free recovery provides a quick return to normal bowel function. Unlike traditional surgery where a major portion of the large intestine is removed, with TAMIS the surgeon will precisely remove the diseased tissue, leaving the rest of the natural bowel lumen intact to function normally. Traditional surgery often requires a large incision and a hospital stay ranging from a few days to more than a week. A TAMIS procedure may only require an overnight stay in the hospital or can be performed as an outpatient procedure, often permitting patients an immediate return to an active lifestyle. TATMe (Trans-anal Total Mesorectal Excision) is a more significant trans-anal procedure.

It would be beneficial to provide a single incision access device having multiple ports with a variety of different port sizes to give a surgeon more options for instrument introduction during a laparoscopic surgical procedure. It would also be beneficial to provide an access device having multiple ports with a variety of different port sizes that enables ready access to natural orifices for performing trans-anal minimally invasive surgical procedures or the like.

SUMMARY OF THE INVENTION

An access device for surgical procedures includes a multiport end cap having a rigid body with a flexible support sealingly mounted to the rigid body with a plurality of separate access ports for accommodating introduction of individual surgical instruments into a body of a patient. At least one of the access ports is sealingly attached to the flexible support and extends in a proximal direction therefrom. The flexible support is of a material more flexible than those of the rigid body and access ports to provide for relative angular movement of at least one of the access ports to provide flexibility for positioning surgical instruments introduced through the access ports.

The flexible support can include at least one flexible bellow. The at least one flexible bellow includes at least one of a rubber material, a rubber-like material, and/or a Versa-Flex material. The rigid body can include a rigid top body and a rigid bellow support, wherein the rigid top body and the rigid bellow support compress an outer peripheral edge of the flexible support therebetween to form a sealing engagement between the rigid body and the flexible support. The rigid bellow support can include at least one support rib extending proximally from the rigid bellow support into the bellow to inhibit inversion of the bellow during instrument insertion into the access port.

The at least one access port can include a compression ring engaged to a distal end of the access port with an inner edge of the flexible support compressed between the access port and the compression ring to form a sealing engagement between the at least one access port and the flexible support. The at least one access port and compression ring can include an axially opposed pair of gripping rims with a portion of the flexible support gripped between the gripping rims. The flexible support can have a respective receptacle groove defined therein for engaging each of the gripping rims. Each of the access ports can include a respective seal configured to seal against gas flow when no surgical instrument is introduced therethrough, and to seal around surgical instruments introduced therethrough.

There can be three access ports extending proximally from the end cap. At least one of the access ports can connect to the rigid body through the flexible support, wherein the flexible support has a single bellow. Two of the access ports can connect to the rigid body through the flexible support, wherein the flexible support has two bellows, one for each of the two access ports. The rigid support can include a respective support rib extending proximally from the rigid support into each one of the two bellows, respectively, to inhibit inversion of the two bellows during instrument insertion into the access port. A second flexible support can be included with a single bellow for connecting a third one of the three access ports to the rigid body. It is also contemplated that the three access ports can connect to the rigid body through the flexible support, wherein the flexible support has three bellows, one for each of the three access ports. The rigid support can include a respective support rib extending proximally from the rigid support into each one of the two bellows, respectively, to inhibit inversion of the two bellows during instrument insertion into the access port.

The flexible support can include a bellow with a single sigmoidal cross-section that positions a distal end of the at least one access port within the multiport end cap. The flexible support can include a bellow with an accordion cross-section that spaces a distal end of the at least one access port proximally from the multiport end cap. The flexible support can include a bellow with a perimeter shape about the at least one access port that includes at least one of round and diamond shaped.

A bottom body can be included having a distally extending tubular body with an access channel defined therethrough for accommodating surgical instruments from the access ports into the body of a patient. The bottom body can include a gas inlet in fluid communication with the access channel. The access ports can be configured to form a mechanical seal for insufflation gas for when instruments are inserted through the access ports and when no instruments are inserted through the access ports. The tubular body can be configured for introduction through a body lumen or through a single incision formed in the wall of the abdominal cavity of a patient. The tubular body can be configured for trans-anal introduction. The end cap can be configured for complete 360° axial rotation relative to the bottom body. The tubular body can be mounted to a main ring portion of the bottom body, wherein the tubular body is of a less rigid material than that of the main ring portion. The rigid body can include at least one flexible tab configured to engage and disengage the bottom body to selectively permit or prevent relative axial rotation of the multiport end cap and bottom body.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 1 is a perspective view of an exemplary embodiment of an access device constructed in accordance with the present disclosure, showing the flexible tab and teeth configured to selectively permit or prevent relative axial rotation of the multiport end cap;

FIG. 2 is an exploded perspective view of the access device of FIG. 1, showing the multiport end cap removed from the bottom body;

FIG. 19 is a perspective view of another exemplary embodiment of an end cap constructed in accordance with the present disclosure, showing a single flexible support with three bellows;

FIG. 20 is an exploded perspective view of the end cap of FIG. 19, showing a rigid bellow support with support ribs to inhibit inversion of the bellows;

FIG. 21 is a perspective view of the triple bellow of FIG. 19;

DETAILED DESCRIPTION OF THE PREFERRED EMBODIMENTS

Figure 3:
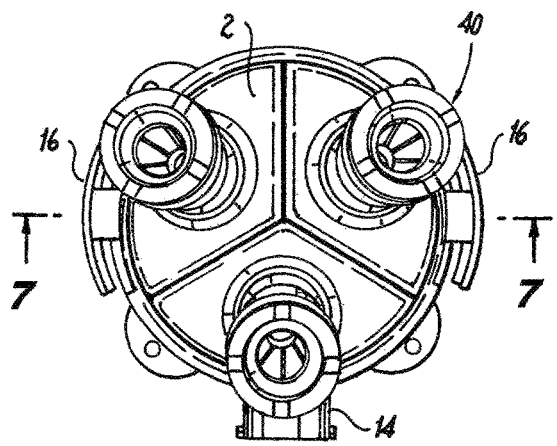
FIG. 3 is a plan view of the access device of FIG. 1, showing the two opposed flexible tabs viewed looking distally.
Figure 4:
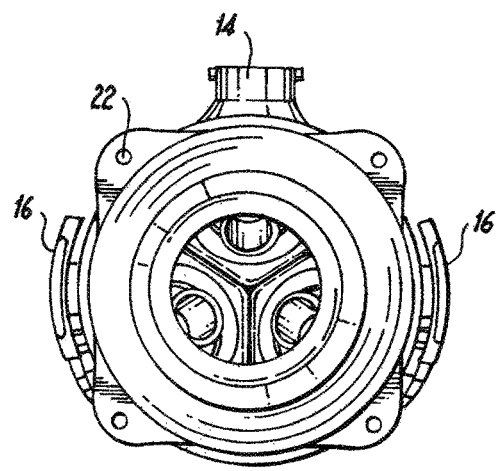
FIG. 4 is a plan view of the access device of FIG. 1, showing the two opposed flexible tabs viewed looking proximally.

Reference will now be made to the drawings wherein like reference numerals identify similar structural features or aspects of the subject disclosure. For purposes of explanation and illustration, and not limitation, a partial view of an exemplary embodiment of an access device in accordance with the disclosure is shown in FIG. 1 and is designated generally by reference character 10. Other embodiments of access devices in accordance with the disclosure, or aspects thereof, are provided in FIGS. 2-34, as will be described. The systems and methods described herein can be used for single incision/natural orifice surgical access, such as for trans-anal minimally invasive surgical procedures, with multiple ports. Commonly assigned U.S. Patent Application Publication Nos. 2016/0287817 and 2017/0056064 are incorporated by reference herein in their entireties. U.S. Patent Application Publication No. 2017/0050011 is incorporated by reference herein in its entirety.

The access device 10 for surgical procedures includes a multiport end cap 20 and a bottom body 30. The end cap includes a plurality of separate access ports 40 for accommodating introduction of individual surgical instruments into a body of a patient. The access ports 40 extend in a proximal direction, i.e., upwards as oriented in FIG. 1. The bottom body 30 has a distally extending, i.e. downward extending as oriented in FIG. 1, tubular body 8 with an access channel 9, shown in FIGS. 6-7, defined therethrough for accommodating surgical instruments from the access ports 40 into the body of a patient. The tubular body 8 is mounted to a main ring portion 6 of the bottom body 30. The tubular body 8 is of a less rigid material than that of the main ring portion 6. The tubular body 8 is configured for introduction into a patient's body, e.g., for trans-anal introduction, or through a single incision formed in the wall of the abdominal cavity of a patient. The bottom body 30 includes suture tie downs 22, which are identified in FIG. 4. After the tubular body 8 of bottom body 30 is inserted into a body cavity or incision, the end cap 20 can be attached to the bottom body 30 to provide gas seal functionality.

Figure 5:
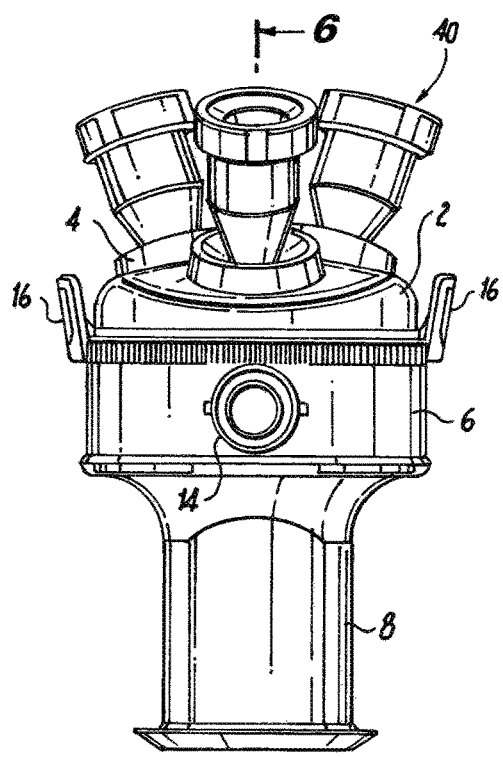
FIG. 5 is a side elevation view of the access device of FIG. 1, showing a connection port for a tube set.
Figure 6:
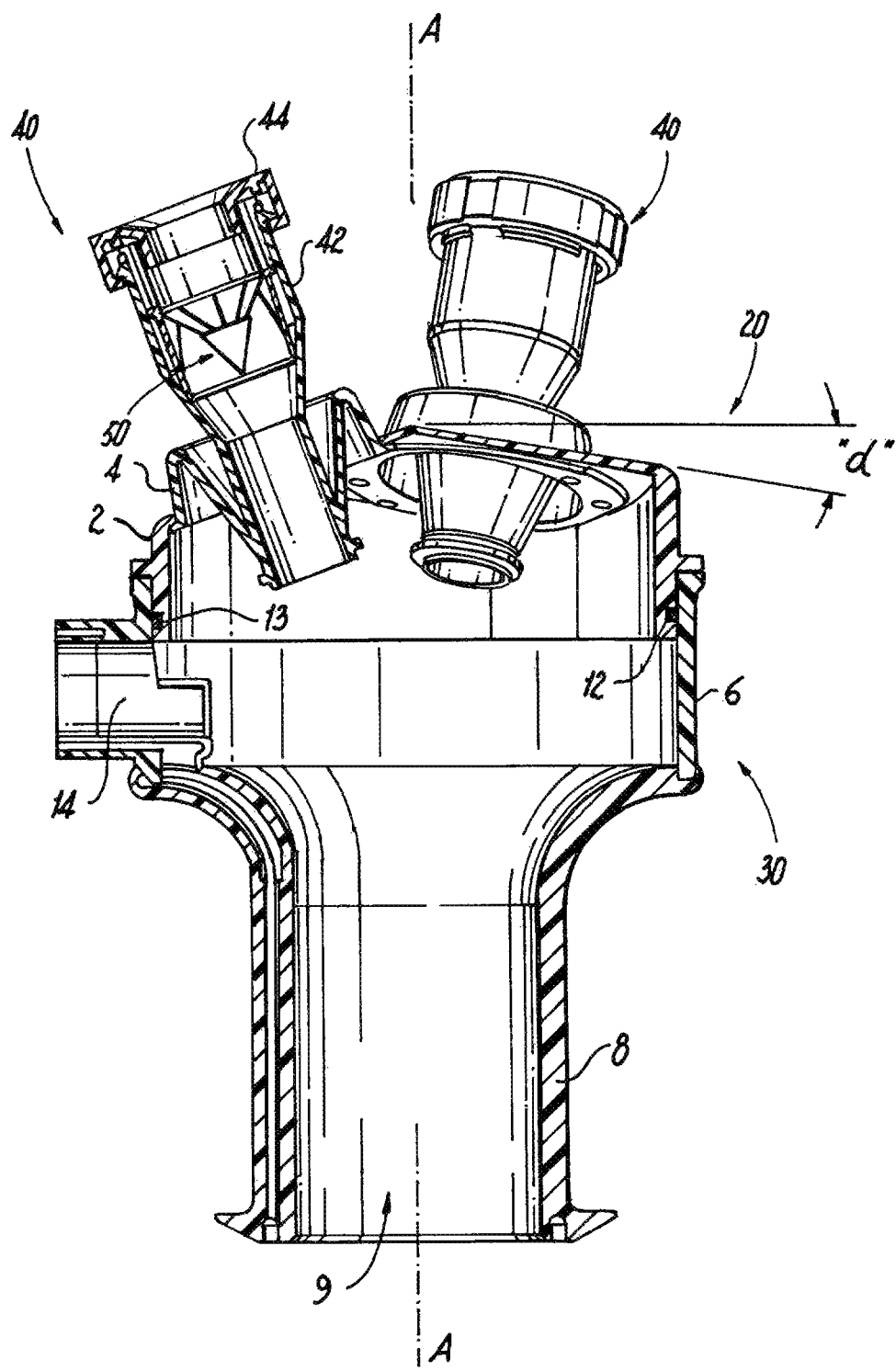
FIG. 6 is a cross-sectional side elevation view of the access device of FIG. 1, showing the sealing ring of the end cap sealing against the proximal rim of the bottom body.

The bottom body 30 includes an insufflation gas inlet 14 in fluid communication with the access channel 9 through tubular body 8. The insufflation gas inlet 14 shown in FIG. 5 is configured to receive a tube set with one or more lumens, e.g., a double lumen tube set, however those skilled in the art will readily appreciate that any other suitable type of inlet can be used without departing from the scope of this disclosure. The access ports 40 are configured to form mechanical seals for insufflation gas for when instruments are inserted through the access ports 40, and when there are no instruments inserted through the access ports 40.

With reference now to FIG. 2, the end cap 20 includes a distally extending seal ring 2. The seal ring 2 of the end cap 20 is received inside and seals against a proximal rim 3 of the bottom body 30. The end cap 20 includes a radially protruding stopper rim 5 that abuts a proximal most surface 19 of bottom body 30. An elastomeric seal ring 12 forms a seal between the seal ring 2 of the end cap 20 and the proximal rim 3 of the bottom body 30 to provide sealing even during relative rotation of the end cap 20 and bottom body 30 about the longitudinal axis A. The elastomeric seal 12 is seated in a circumferential channel 13 defined in the seal ring 2.

Figure 10:
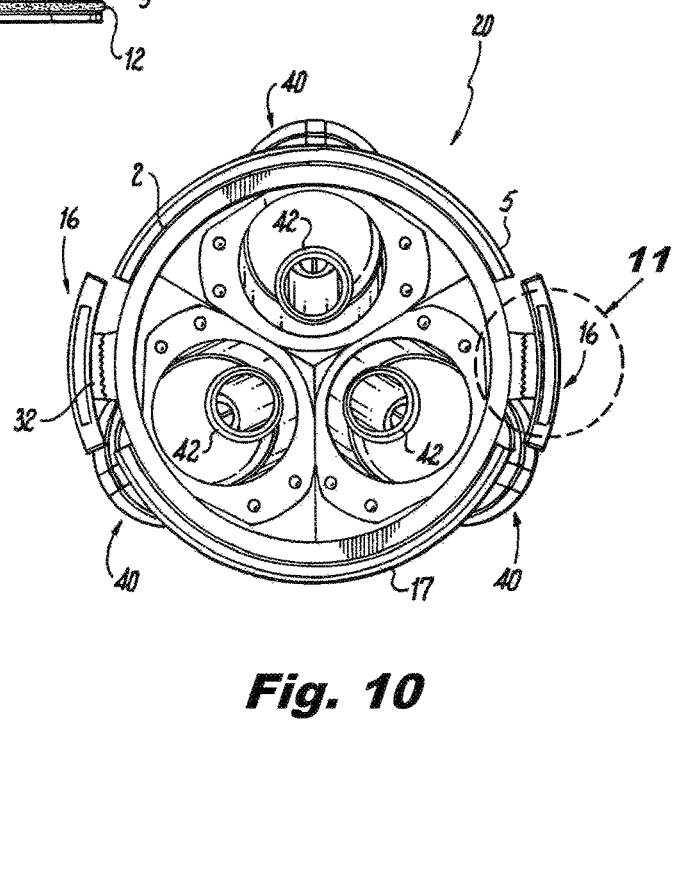
FIG. 10 is a plan view of the end cap of FIG. 8, showing the teeth of the flexible tabs.
Figure 11:
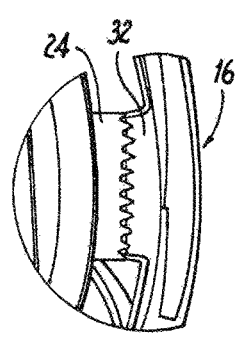
FIG. 11 is a plan view of a portion of the end cap of FIG. 8, showing the teeth of one of the flexible tabs.

The bottom body 30 includes a plurality of circumferentially spaced apart teeth 18 on the outside of the proximal rim 3. The end cap 20 includes an opposed pair of flexible tabs 16, shown in FIGS. 3-4, with distal teeth 32 thereon that extend radially inward, as shown in FIGS. 10 and 11, configured to engage and disengage the radially outwardly extending teeth 18 of the bottom body 30 to selectively permit or prevent relative axial rotation of the multiport end cap 20 around the longitudinal axis A.

Figure 7:
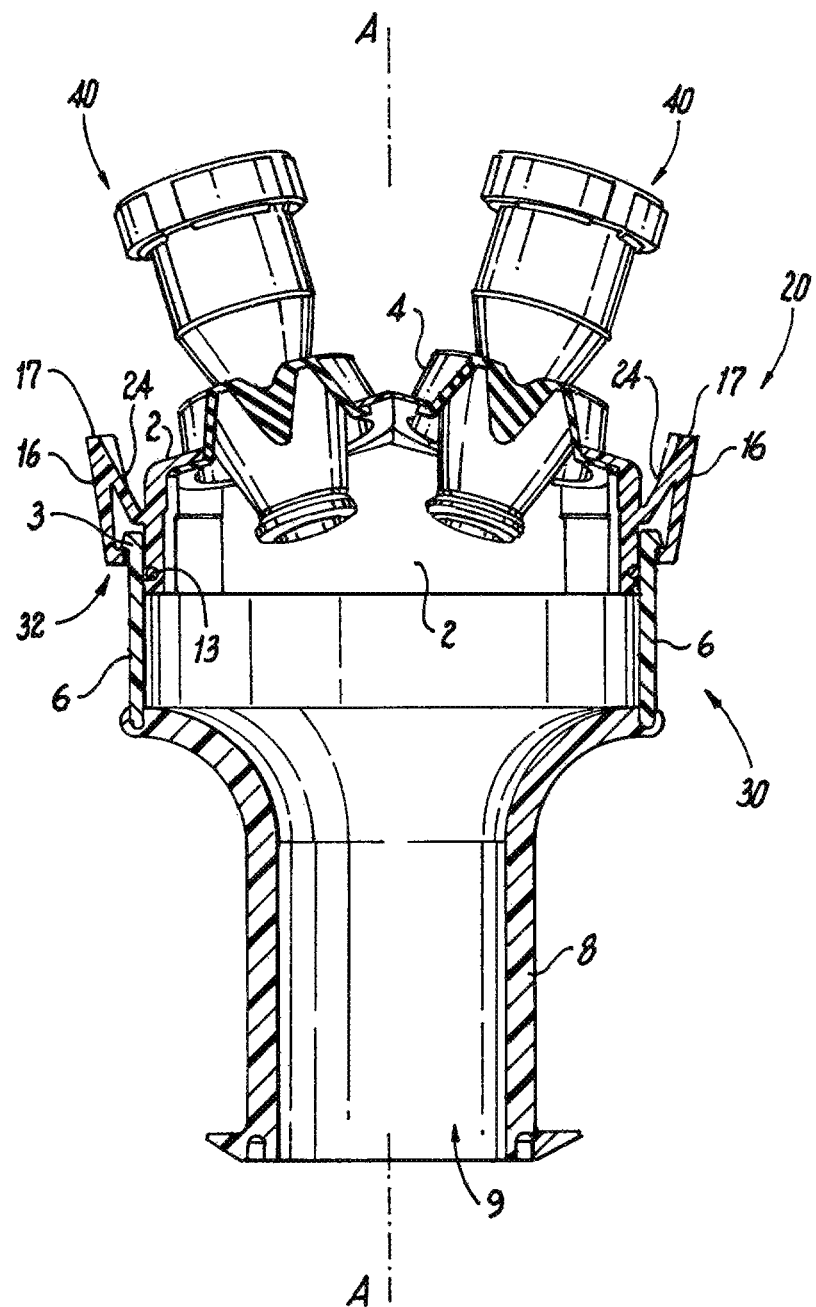
FIG. 7 is a cross-sectional side elevation view of the access device of FIG. 1, showing the flexible tabs engaging the teeth of the bottom body.
Figure 8A:
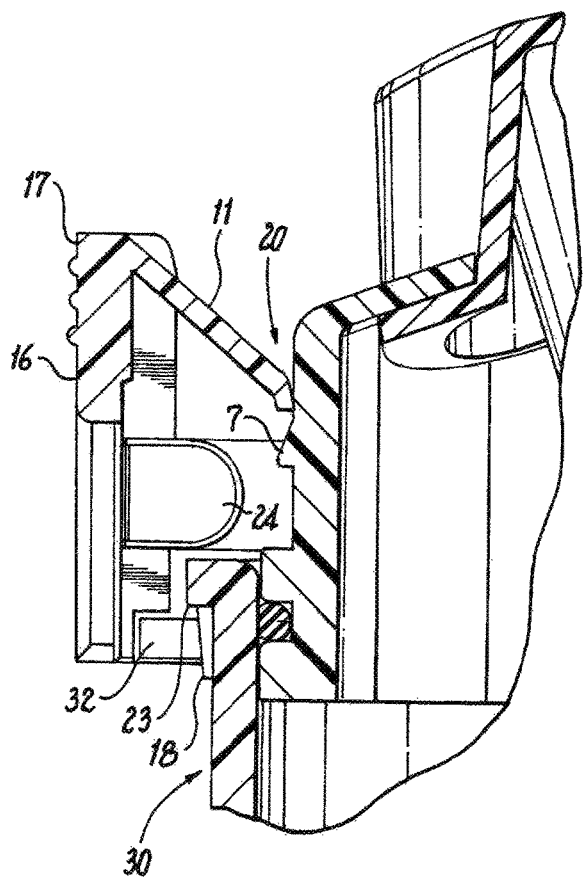
FIG. 8A is a cross-sectional side elevation view of a portion of the access device of FIG. 1, showing a pivoting hinge instead of compliant hinge for the flexible tabs.

With reference now to FIGS. 7 and 8A, each of the flexible tabs 16 includes a proximally extending manipulation member 17 and a compliant hinge member 24 between the manipulation member and the distal teeth 32 of the flexible tab 16. In FIG. 7, hinge member 24 is shown as a compliant hinge member, however it can also be a pivoting hinge member 24 as shown in FIG. 8A. The flexible tabs 16 are integral with the end cap 20, and are connected to the end cap 20 by the complaint hinge members 24. Since there are there are two circumferentially opposed flexible tabs 16, squeezing the manipulation members 17 together, i.e., radially inward towards one another, releases the teeth 32 of the flexible tabs 16 from the teeth 18 of the bottom body 30 to allow rotation of the end cap 20 relative to the bottom body 30 around the longitudinal axis A. The end cap 20 is configured for complete 360° axial rotation relative to the bottom body 30. Releasing the flexible tabs 16 re-engages the teeth 18 and 32 to prevent further rotation. The bottom body 30 includes a latching surface 23, labeled in FIG. 8A, proximal to the teeth 18 thereof. The flexible tabs 16 latch with the latching surface 23 to prevent axial movement of the end cap away from the bottom body when the teeth 18 and 32 are engaged, and can even stay latched when the teeth 18 and 32 are disengaged during relative axial rotation of the end cap 20 and the bottom body 30 to prevent axial displacement of the end cap 20 relative to the bottom body 30 during rotation. Optional feedback member 11 cams against the cam 7 to increase force feedback as a user squeezes manipulation members 17 to prevent over squeezing to keep latching surface 23 engaged to the teeth 32 when rotating end cap 20 without axially removing it from bottom body 30. The proximal rim 3 is sandwiched between the seal ring 2 and teeth 32 of end cap 20, as shown in the cross-section of FIG. 7.

Figure 8B:
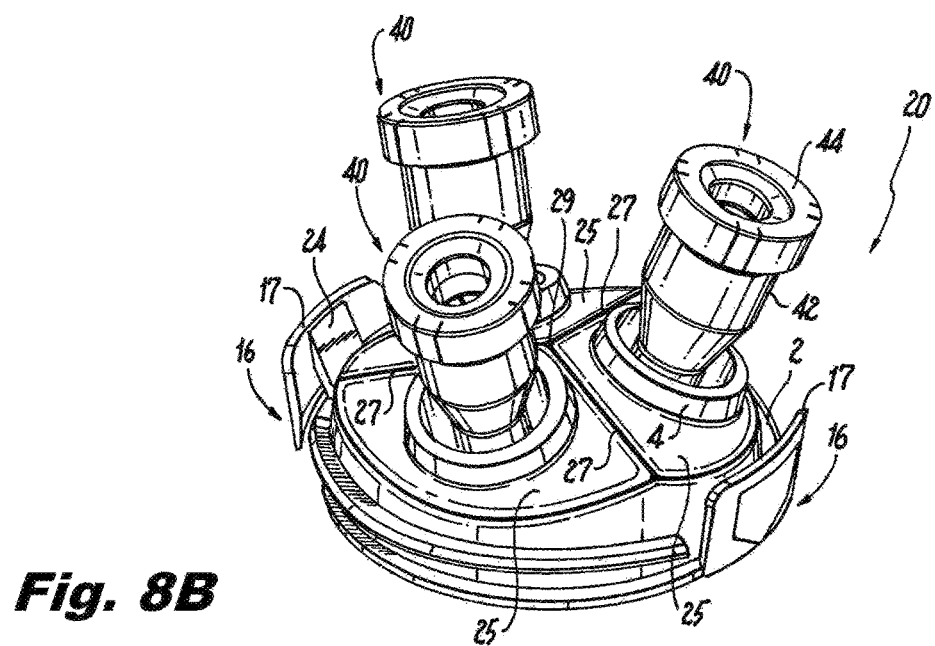
FIG. 8B is a perspective view of a portion of the access device of FIG. 1, showing the end cap.

With reference now to FIG. 8B, there are three access ports 40 extending proximally from the end cap 20. As shown in FIGS. 3 and 10, the access ports 40 are evenly spaced circumferentially about the end cap 20, and all three access ports 40 can be of a uniform size with one another, or can vary in size. Each access port 40 includes a rigid cannula body 42 and a cannula cap 44 housing a seal assembly 50, shown in FIG. 6, for sealing against surgical instruments passing through the respective access port 40. Each cannula body 42 is permanently attached in an air tight manner to a bellow 4, e.g. of an elastomeric material, which is in turn permanently attached in an air tight manner to the respective facet 25 of end cap 20, e.g., by adhesive, ultrasound welding, over molding, or any other suitable joining process). The flexibility of bellow 4 allows for relative movement of the rigid cannula bodies 42 with respect to one another to provide flexibility and movement for surgical devices inserted through access ports 40.

Figure 9:
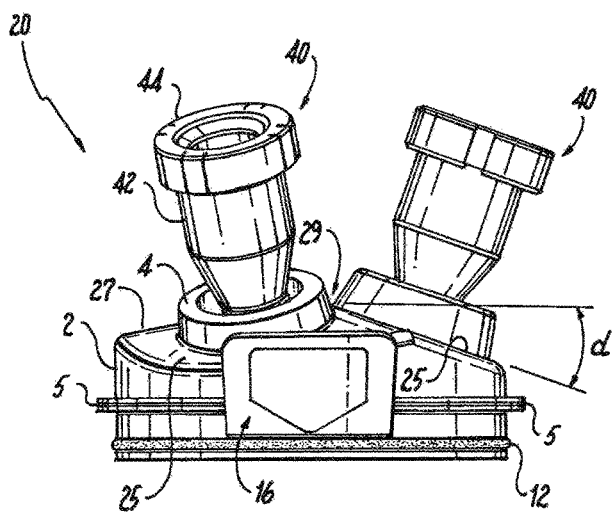
FIG. 9 is a side elevation view of the end cap of FIG. 8, showing the angle of the facet junctures of the end cap.

Each access port 40 extends from a respective planar facet 25 of the end cap 40. Each access port 40 extends normal from the respective facet 25 of the end cap 20. The respective facets 25 meet at facet junctures 27, wherein the facet junctures meet each other at an apex 29 of the end cap 20. As shown in FIG. 9, each facet 25 is angled at an angle α from a circumferential plane of the end cap 20, e.g., relative to a plane parallel to rim 5. The angle α is larger than 0° and less than or equal to 60°.

Figure 12:
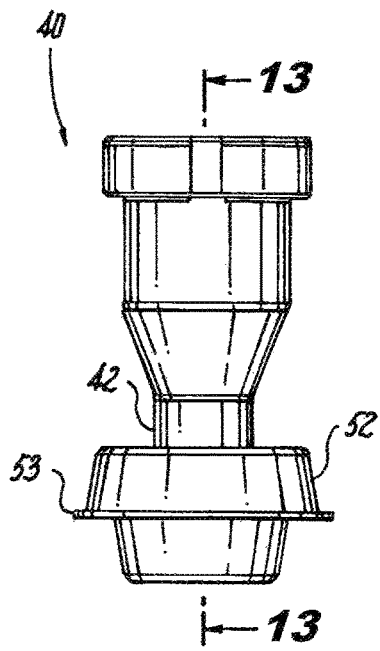
FIG. 12 is a side elevation view of one of the access ports of the end cap of FIG. 8, showing the bellow.
Figure 13:
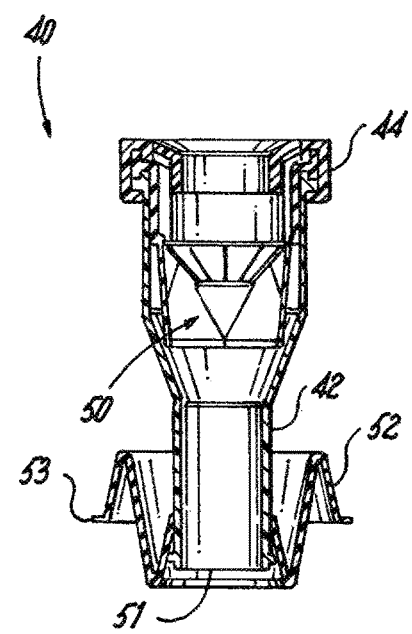
FIG. 13 is a cross-sectional side elevation view of the access port of FIG. 12, showing the cross-section of the bellow.

With reference now to FIG. 12, an access port with another embodiment of a bellow 52 is shown, wherein the base 53 of the bellow 52 is circular. As shown in FIG. 13, bellow 52 forms a flexible support with a single sigmoidal cross-section that positions a distal end 51 of the at least one access port 40 within the multiport end cap, represented in FIG. 13 by the dashed line, and as shown in the cross sections of FIGS. 6 and 7. The flexible supports, e.g., including bellows 52, described herein can include at least one of a rubber material, a rubber-like material, and/or a VersaFlex material available from VersaFlex Incorporated of Kansas City, Kans.

Figure 14:
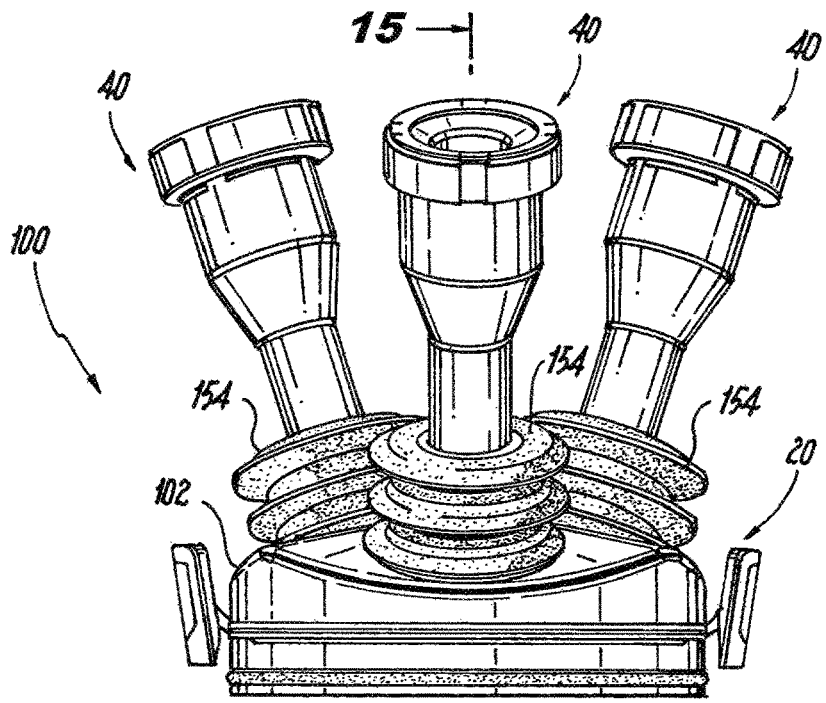
FIG. 14 is a side elevation view of another embodiment of an end cap constructed in accordance with the present disclosure, showing bellows with accordion cross-sections.
Figure 15:
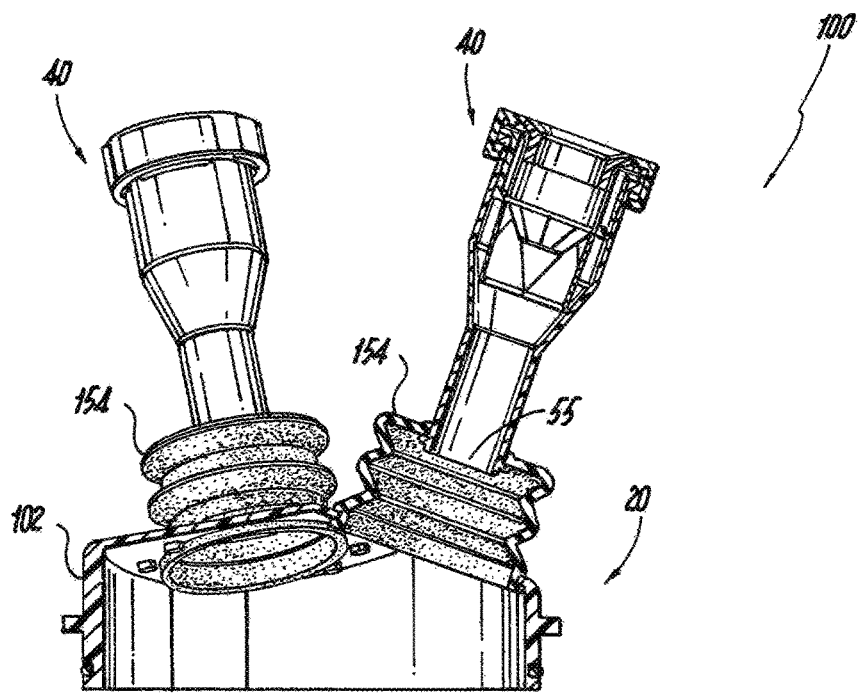
FIG. 15 is a cross-sectional side elevation view of the end cap of FIG. 14, showing the cross-section of one of the bellows.

Referring now to FIG. 14, another exemplary embodiment of an access device 100 for surgical procedures includes a multiport end cap 120 having a rigid body 102 with flexible supports 154 sealingly mounted to the rigid body 102 with a plurality of separate access ports 40 for accommodating introduction of individual surgical instruments into a body of a patient, much as described above with respect to access device 10. Each of the access ports 40 is sealingly attached to a respective one of the flexible supports 154 and extends in a proximal direction therefrom, i.e., in an upwards direction as oriented in FIG. 14. The flexible supports 154 are of a material more flexible than those of the rigid body 102 and access ports 40 to provide for relative angular movement of the access ports 40 to provide flexibility for positioning surgical instruments introduced through the access ports 40. Each of the flexible supports 154 includes a flexible bellow with an accordion cross-section, as shown in FIG. 15, which spaces a distal end 55 of the respective access port 40 proximally from the multiport end cap 20.

Figure 16:
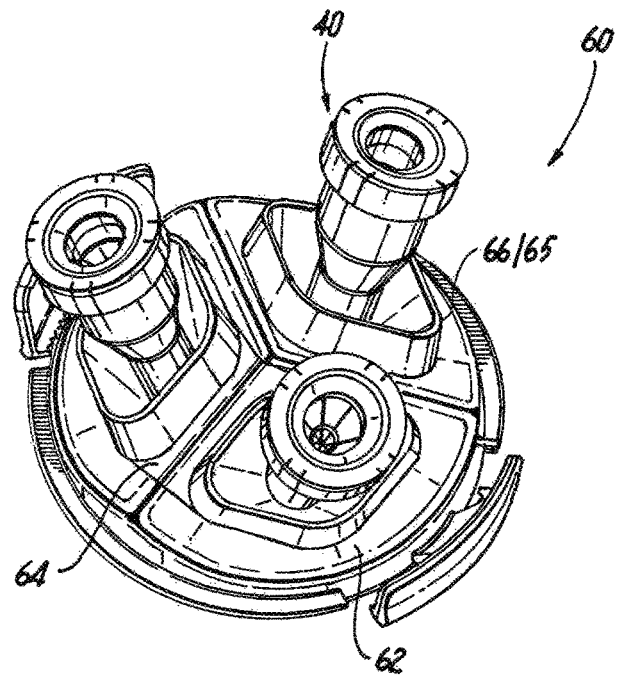
FIG. 16 is a perspective view of another exemplary embodiment of an end cap constructed in accordance with the present disclosure, showing two flexible supports, one including a single bellow and one including a double bellow.
Figures 17, 18:
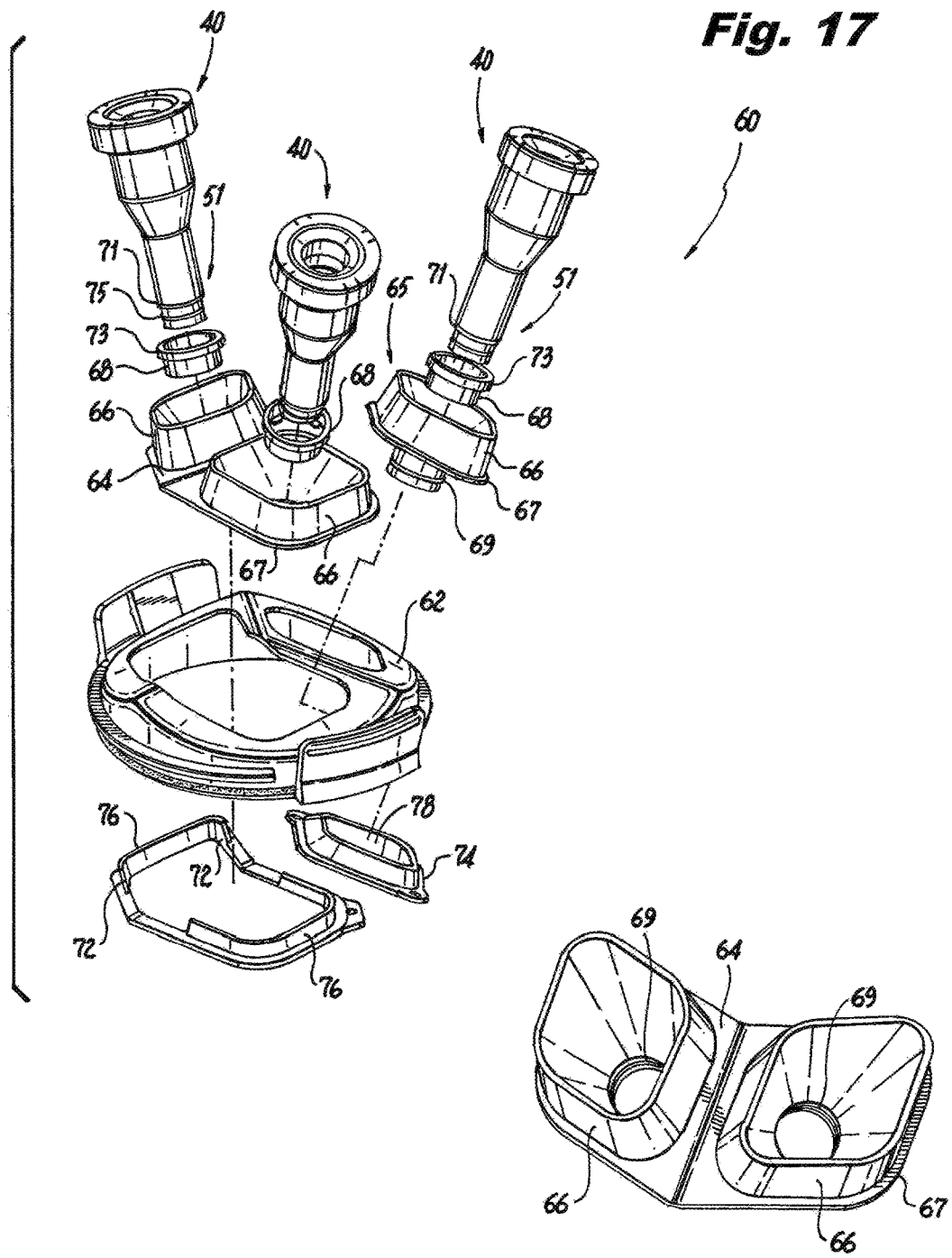
FIG. 17 is an exploded perspective view of the end cap of FIG. 16, showing rigid bellow supports with support ribs to inhibit inversion of the bellows.
FIG. 18 is a perspective view of the double bellow of FIG. 16.

With reference now to FIG. 16, another exemplary embodiment of an end cap 60 is shown. Whereas the bellows 52 and 154 in FIGS. 12-15 have a perimeter shape about the respective access ports that is round, in end cap 60, the bellows 66 have diamond shaped perimeters around the respective access ports 40. As shown in FIG. 17, the rigid body of end cap 60 includes a rigid top body 62 and a two rigid bellow supports 72 and 74. The rigid top body 62 and the rigid bellow supports 72 and 74 compress an outer peripheral edge 67 of the flexible supports 64 and 65 therebetween axially, e.g., by ultrasound welding, adhesive, or any other suitable joining technique, to form a sealing engagement between the rigid body of the end cap 60 and the flexible supports 64 and 65. The rigid bellow supports 72 and 74 each include a respective support rib 76 and 78 extending proximally from the rigid bellow support 72 and 74 into the respective bellow 66 to inhibit inversion of the bellow 66 during instrument insertion into the access port 40.

Each access port 40 can include a compression ring 68 engaged to the distal end 51 of the access port 40. An inner edge 69 of the flexible supports 64 and 65 compressed between the respective access port 40 and the compression ring 68 to form a sealing engagement between the access ports 40 and the flexible supports 64 and 65. Each paired access port 40 and compression ring 68 include an axially opposed pair of respective gripping rims 71 and 73 with a portion of the respective flexible support 64 and 65 gripped between the gripping rims 71 and 73. Each flexible support has a respective receptacle groove 75 defined therein for engaging each of the gripping rims 71 and 73. Each of the access ports 40 includes a respective seal, much like seal assembly 50 described above, configured to seal against gas flow when no surgical instrument is introduced therethrough, and to seal around surgical instruments introduced therethrough.

As with end cap 20 described above, end cap 60 includes three access ports 40 extending proximally from the end cap 60. One of the access ports 40 connects to the rigid body of end cap 60 through the flexible support 65, wherein the flexible support 65 has a single bellow 66. The remaining two access ports 40 connect to the rigid body of end cap 60 through the flexible support 64, wherein the flexible support 64 has two bellows 66, i.e., a double bellow, as shown in FIG. 18, one for each of the two access ports 40.

With reference again to FIG. 17, the rigid bellow support 72 of the rigid support includes two respective support ribs 76 extending proximally from the rigid support 72 into each one of the two bellows 66, respectively, to inhibit inversion of the two bellows 66 during instrument insertion into the access port 40. The rigid bellow support 74 includes a single support rib 76 extending proximally from the rigid support 74 into the respective bellow 66 for the same purpose.

Referring now to FIG. 19, another exemplary embodiment of an end cap 80 much like end caps 20 and 60 described above is shown with diamond shaped bellows 66. The three access ports 40 connect to the rigid body of end cap 80 through the flexible support 84, wherein the flexible support 84 has three bellows 66, i.e., a triple bellow as shown in FIG. 21, one for each of the three access ports 40. As shown in FIG. 20, the rigid body of end cap 80 includes a rigid top body 82 and a single rigid bellow support 86. The rigid top body 82 and the rigid bellow support 86 compress an outer peripheral edge 87 of the flexible support 84 therebetween to form a sealing engagement between the rigid body of the end cap 80 and the flexible support 84. Three respective support ribs 88 extending proximally from the rigid support 86 into each one of the three bellows 66, respectively, to inhibit inversion of the bellows 66 during instrument insertion into the access ports 40.

Figure 22:
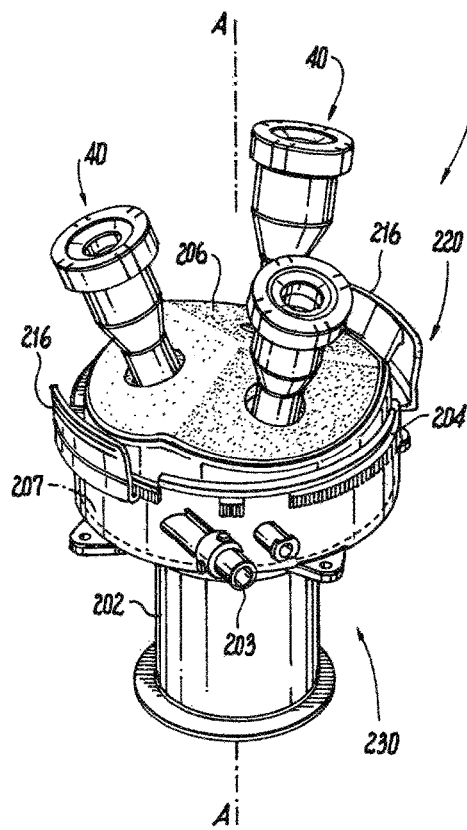
FIG. 22 is a perspective view of another exemplary embodiment of an end cap constructed in accordance with the present invention, showing a flexible body that includes a flexible foam material.

With reference now to FIG. 22, another exemplary embodiment of an access device 200 is shown for surgical procedures. Access device 200 includes a multiport end cap 220 having a rigid body 204 with a flexible support 206 sealingly mounted to the rigid body 204 with a plurality of separate access ports 40 as described above for accommodating introduction of individual surgical instruments into a body of a patient.

A bottom body 230 is included in the access device 200, having a distally extending tubular body 202 with an access channel defined therethrough for accommodating surgical instruments from the access ports 40 into the body of a patient as in embodiments described above. The bottom body 230 includes a connection port 203 for connecting a tube set with one or more lumens in fluid communication with the access channel much as described above with respect to access device 10. The access ports 40 are configured to form mechanical seals for insufflation gas for when instruments are inserted through the access ports 40, and when there are no instruments inserted though the access ports 40. The tubular body 202 is mounted to a main ring portion 207 of the bottom body 230, and wherein the tubular body 202 is of a less rigid material than that of the main ring portion 207. The tubular body 202 is configured for introduction through a natural orifice of a body lumen or through a single incision formed in the wall of the abdominal cavity of a patient, for trans-anal introduction, or any other suitable mode of introduction.

As in embodiments described above, the end cap 220 is configured for complete 360° axial rotation relative to the bottom body 230 about longitudinal axis A. The rigid body includes at least one flexible tab 216 configured to engage and disengage the bottom body 230 to selectively permit or prevent relative axial rotation of the multiport end cap 220 and bottom body 230 as described above with respect to access device 10. Each of the access ports 40 includes a respective seal assembly as described with respect to embodiments above.

The access ports 40 are sealingly attached to the flexible support 206 and extend in a proximal direction therefrom, i.e. upwards as oriented in FIG. 22. The flexible support 206 is of a material more flexible and/or stretchable than those of the rigid body 204 and access ports 40 to provide for relative angular movement of the access ports 40 to provide flexibility for positioning surgical instruments introduced through the access ports.

Figure 23:
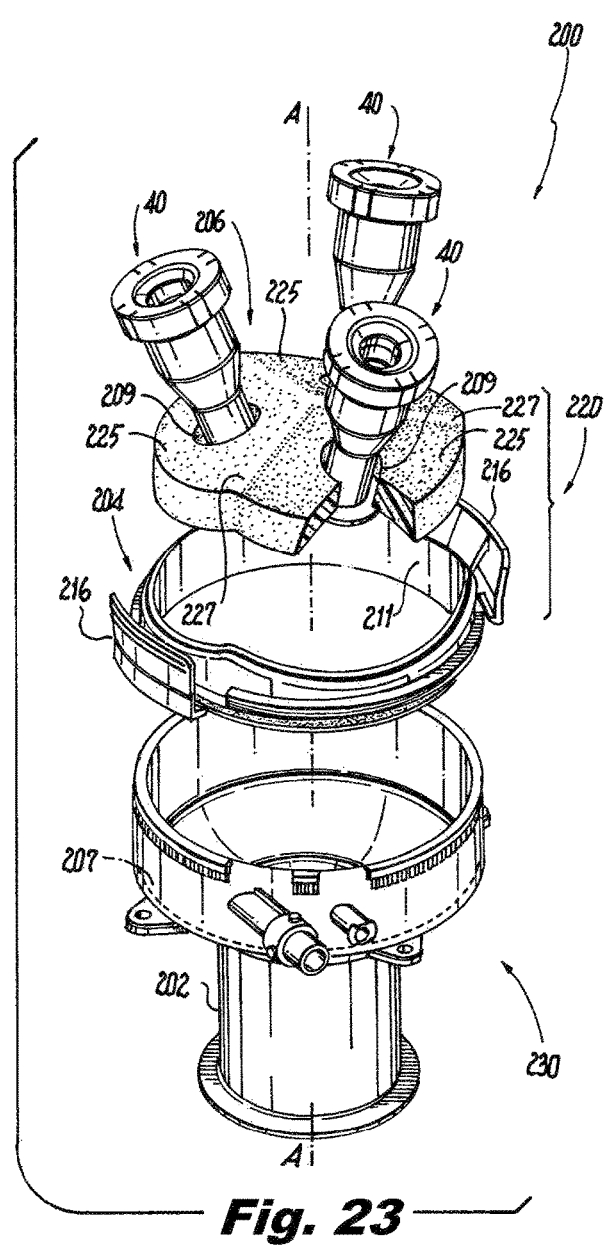
FIG. 23 is an exploded perspective view of the end cap of FIG. 22, showing the rigid body separated from the flexible foam support.

With reference now to FIG. 23, the flexible support 206 includes a flexible, closed-cell foam material for providing sealing to prevent gas flow therethrough; however it is also contemplated that an open-cell foam material can be used with an air tight coating. It is also contemplated that the foam material can include at least one of a rubber material, a rubber-like material, a VersaFlex material available from VersaFlex Incorporated of Kansas City, Kans., and/or a foam material made from a gel or gel-like material. The access ports 40 are mounted to a distal surface of the flexible support 206, i.e. the bottom surface of flexible support 206 as oriented in FIG. 23, and extend proximally through respective bores 209 in the flexible support 206 to extend proximally from the flexible support 206. The rigid body 204 defines a complete circumferential ring wherein the flexible support 206 is mounted within and spans the circumferential ring forming a complete circumferential seal between the rigid body 204 and the flexible support 206. The flexible support 206 is adhered, ultrasonic welded, clamped or joined by any other suitable joining technique to an inward facing surface 211 of the circumferential ring to form a gas tight seal between the flexible support 206 and the rigid body 204.

Figure 34:
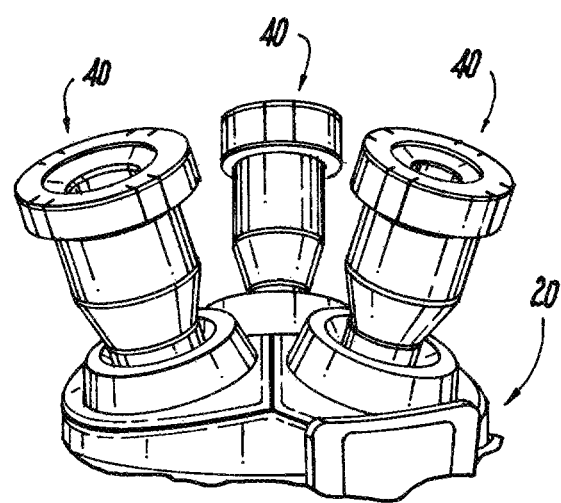
FIG. 34 is a schematic view of the access device of FIG. 1, showing access ports 40 that vary in size relative to one another.

As with embodiments described above, there are three access ports 40 extending proximally from the end cap 220, evenly spaced circumferentially about the end cap 220, and uniform in size with one another, however it is also contemplated that in an end cap can have ports of sizes that differ from one another as shown schematically in FIG. 34. Each access port 40 extends from a respective planar facet 225 of the flexible support 206. Each access port 40 extends normal from the respective facet 225 of the flexible support. The respective facets 225 meet at facet junctures 227, wherein the facet junctures 227 meet each other at an apex 229 of the flexible support 206. Each facet 225 is angled at an angle α from a circumferential plane of the end cap 220. The angle α is not labeled in FIG. 23, but see angle α labeled in FIG. 9 as described above. The angle α is larger than 0° and less than or equal to 60°. It is also contemplated that the flexible support 206 can be flat, e.g. where angle α is equal to 0°.

Figure 24:
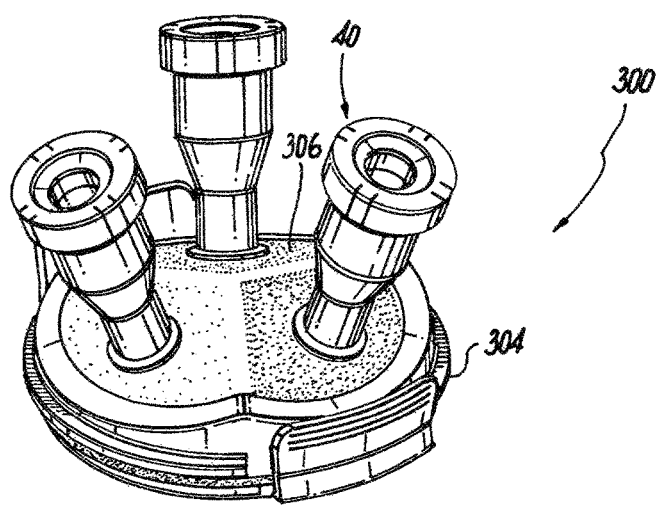
FIG. 24 is a perspective view of another exemplary embodiment of an end cap constructed in accordance with the present invention.
Figure 25:
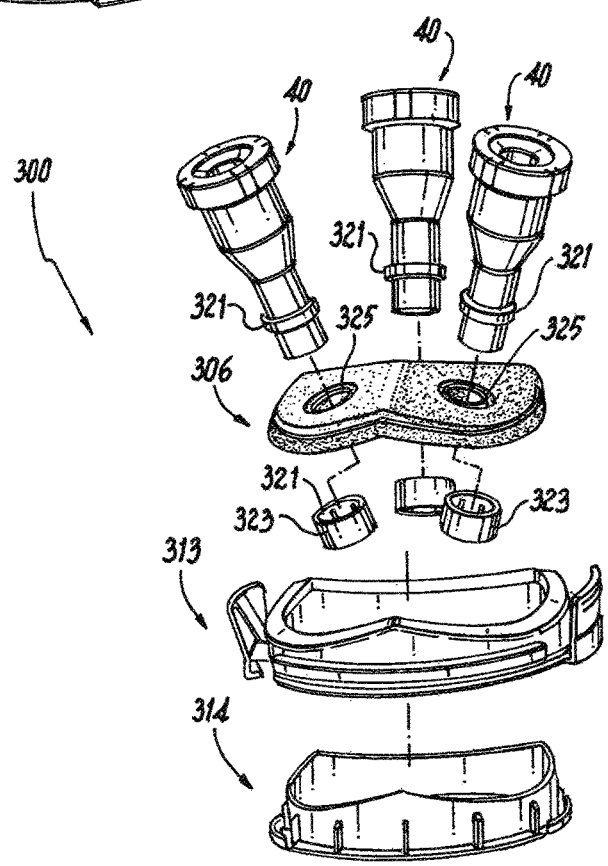
FIG. 25 is an exploded perspective view of the end cap of FIG. 24, showing the access ports separated from the flexible foam support.
Figure 26:
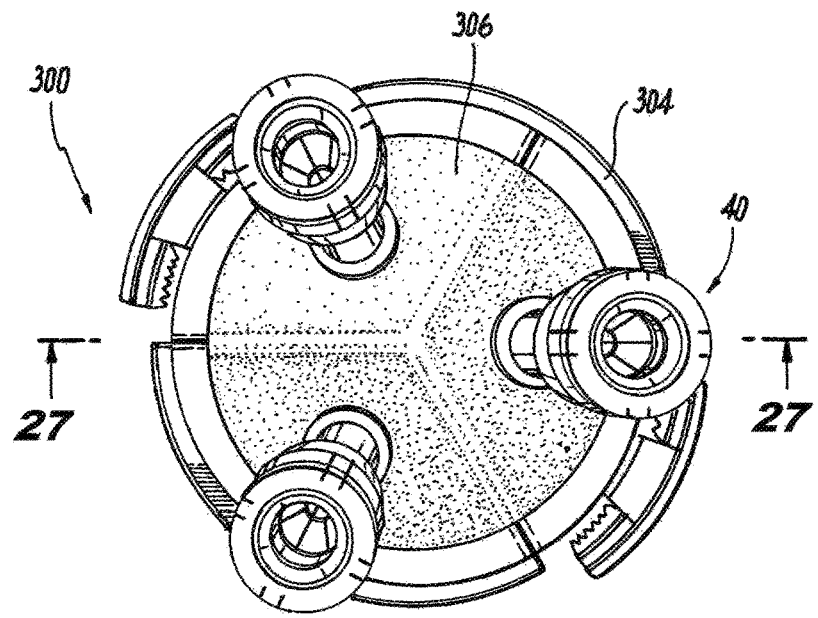
FIG. 26 is a plan view of the end cap of FIG. 24, showing the flexible tabs.
Figure 27:
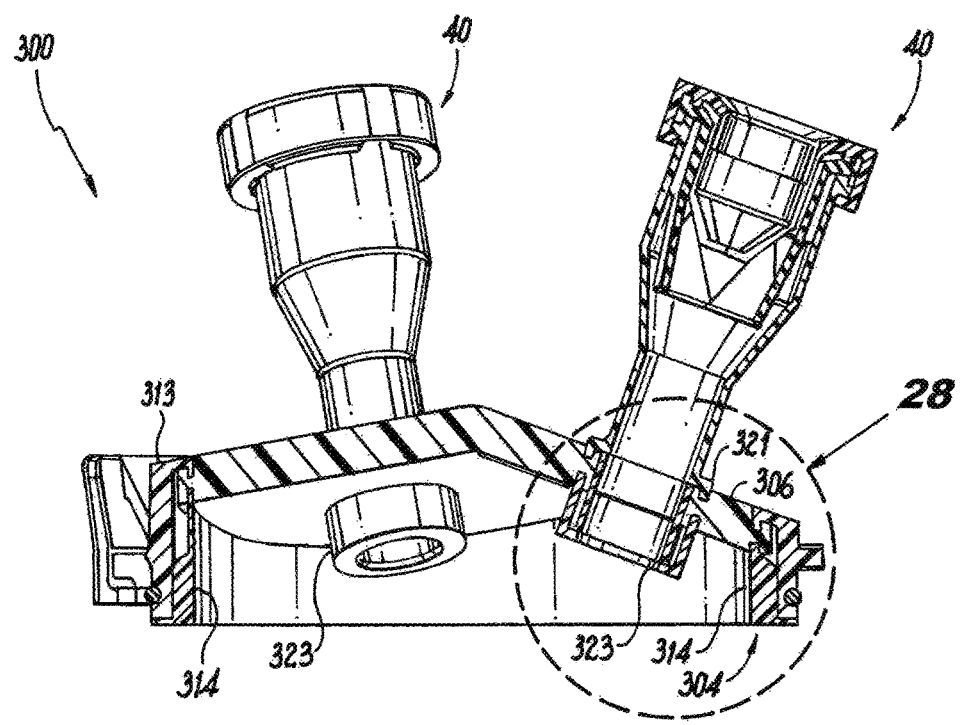
FIG. 27 is a cross-sectional side elevation view of the end cap of FIG. 24, showing the attachment of one of the access ports to the flexible foam support.
Figure 28:
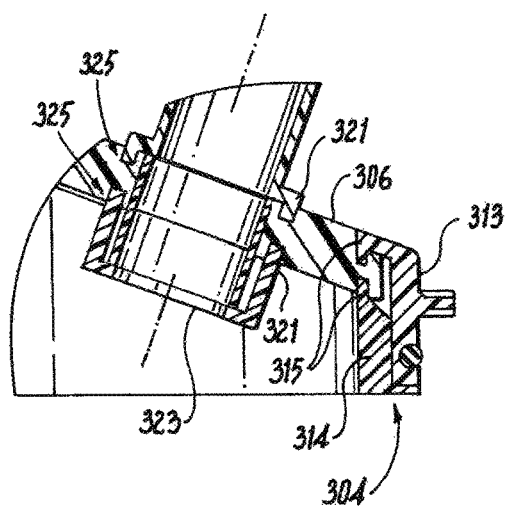
FIG. 28 is a cross-sectional side elevation view of a portion of the end cap of FIG. 24, showing the gripping rims of one of the access ports gripping the flexible support.

With reference now to FIG. 24, another exemplary embodiment of an access device 300 is shown, including a flexible support 306 as described above with respect to access device 200. As shown in FIG. 25, the circumferential ring of rigid body 304 includes a proximal ring portion 313 and a distal ring portion 314. As shown in FIGS. 26-27, the flexible support 306 is squeezed between the proximal and distal ring portions 313 and 314. The flexible support 306 defines a respective ring groove 315 (labeled in FIGS. 25 and 28) in its proximal and distal surfaces for receiving circumferential rims of the proximal and distal ring portions 313 and 314. The proximal and distal portions 313 and 314 can be sealingly joined to the flexible support 306 by ultrasonic welding, adhesive, or any other suitable joining technique.

Each access port 40 includes an axially opposed pair of gripping rims 321, including a proximally extending gripping rim 321 defined on a compression ring 323 joined to the distal end of each access port 40. A portion of the flexible support 306 is gripped between the respective gripping rims 321 of each access port 40. The flexible support 306 has a respective receptacle groove 325 defined therein for receiving each of the gripping rims 321.

Figure 29:
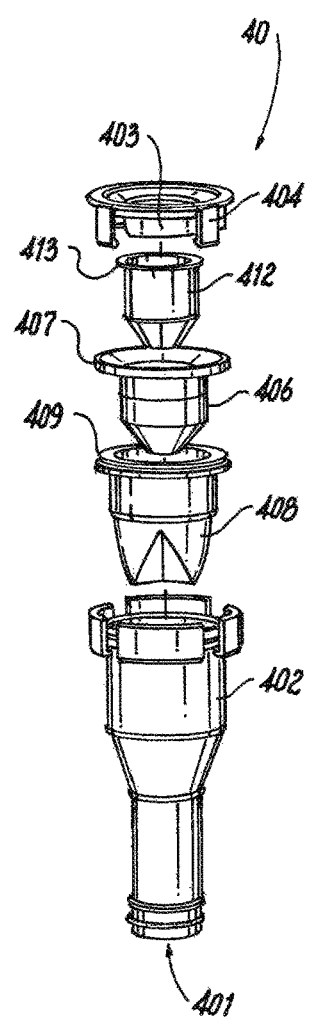
FIG. 29 is an exploded perspective view of one of the access ports constructed in accordance with an exemplary embodiment, showing the seal guard.
Figure 30:
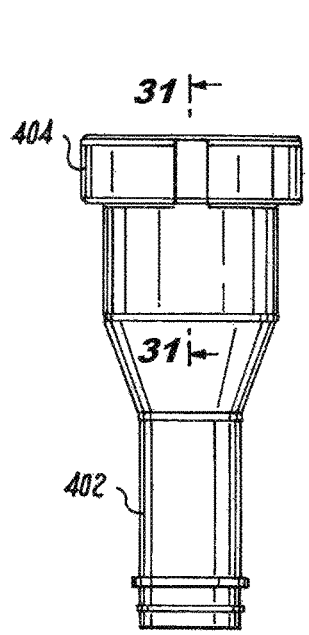
FIG. 30 is a side elevation view of the access port of FIG. 29, showing the cap mounted on the proximal end of the surgical port body.
Figure 31:
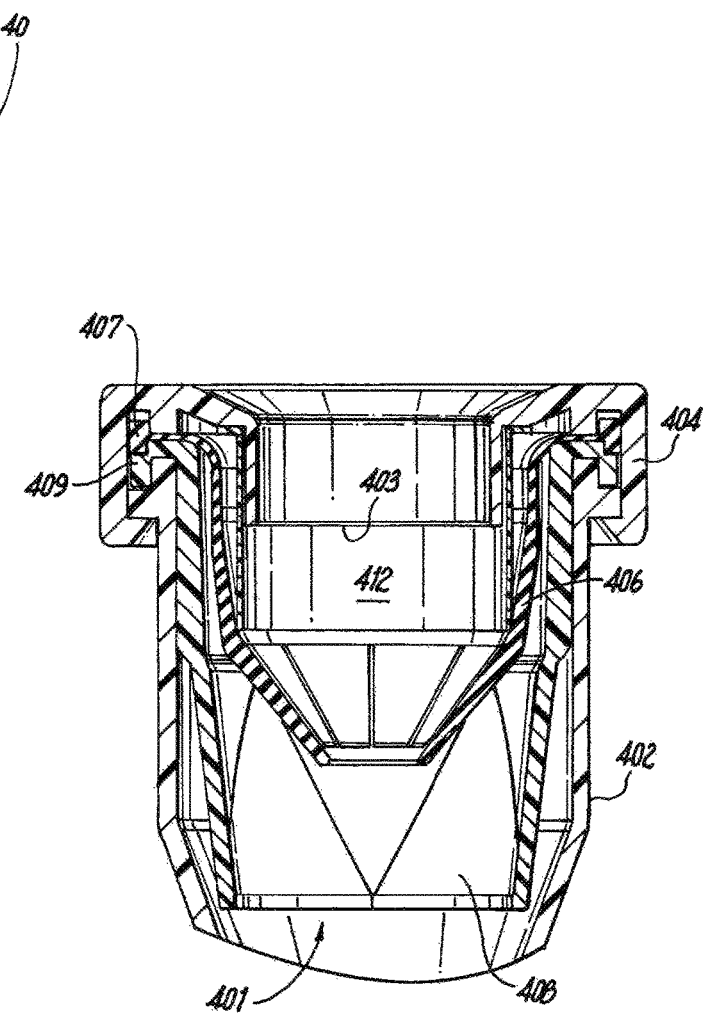
FIG. 31 is a cross-sectional side elevation view of a portion of the access port of FIG. 29, showing the bases of the main and duck bill seals fixed between the cap and the surgical port body with the base of the seal guard floating unfixed relative to the cap and surgical port body.

With reference now to FIG. 29, at least one of the access ports 40 can include a surgical port assembly that provides mechanical sealing for surgical instruments to reduce loss of pressure during surgical procedures. The assembly includes a tubular surgical port body 402 extending from an upper surface of the end cap, e.g., any of the end caps described above, and defining an access channel 401 therethrough. A cap 404 is mounted to a proximal end of the surgical port body 402 and opens into the access channel 401 of the surgical port body 402, as shown in FIGS. 30 and 31. A main seal 406 has a base 407 that is fixed between the cap 404 and the surgical port body 402 to suspend the main seal 406 across the access channel 401 as shown in FIG. 31 to provide mechanical sealing against surgical instruments extending through the access channel 401. A duck bill seal 408 is included distal from the main seal 406 within the access channel 401. The duck bill seal 408 includes a base 409 that is fixed between the cap 404 and the surgical port body 402 and provides mechanical sealing against surgical instruments extending through the access channel 401 in addition to the sealing provided by main seal 406.

A seal guard 412 is seated in an unfixed manner between the cap 404 and the main seal 406 within the access channel 401. The seal guard 412 is of a material that is more rigid that those of the main seal 406 and the duck bill seal 408 to provide protection for the main seal 406 and the duck bill seal 408 when instruments are inserted through access channel 401, and to prevent inversion of the main seal 406 and/or the duck bill seal 408, e.g., when surgical instruments are withdrawn from access channel 401.

With continued reference to FIG. 31, the seal guard 412 extends across the access channel 401 and is configured to move relative to the cap 404 and the surgical port body 402 to accommodate movement of surgical instruments extending through the access channel 401. The seal guard 412 can move relative to the bases 407 and 407 of the main seal 406 and duck bill seal 408. This movement is accommodated by the seating of the base 413 of the seal guard 412 about the inward rim 403 of cap 404 within access channel 401. Since it is free to move relative to the cap 404 and the surgical port body 402, the seal guard 412 can accommodate movement of instruments relative to surgical port body 402 and therefore improve sealing against the instruments by the main seal 406 and duckbill seal 408 relative to the sealing that would be accomplished if the seal guard 412 was rigidly mounted relative to the cap 404 and the surgical port body 402.

Figure 32:
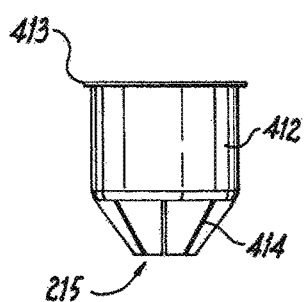
FIG. 32 is a side elevation view of the seal guard of FIG. 29, showing the access slits.
Figure 33:
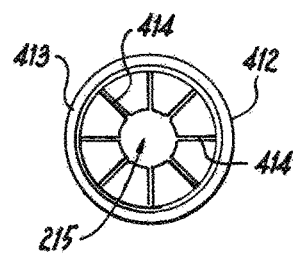
FIG. 33 is distal end view of the seal guard of FIG. 32, showing the circumferential spacing of the access slits.

As shown in FIGS. 32 and 33, the seal guard 412 defines eight evenly spaced access slits 414 therethrough in a distal, frustoconical section of the seal guard 412. The access slits are spaced circumferentially about the central aperture 215 of the seal guard 412 for passage of surgical instruments through the seal guard 412, accommodated by the deflectable panels separated by the access slits 414. The access slits 414 facilitate alignment of surgical instruments with openings through the main seal 406 and the duck bill seal 408 to reduce leakage of pressurized gas through the main seal 406 and duck bill seal 408 during surgery.

The methods and systems of the present disclosure, as described above and shown in the drawings, provide for single incision/natural orifice surgical access with superior properties including minimally invasive, multiple port access with flexibility for relative movement of the access ports. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. An access device for surgical procedures comprising: a multiport end cap including a rigid body with a flexible support sealingly mounted to the rigid body with a plurality of separate access ports for accommodating introduction of individual surgical instruments into a body of a patient, at least one of the access ports sealingly attached to the flexible support and extending in a proximal direction therefrom, wherein the flexible support is of a material more flexible than those of the rigid body and access ports to provide for relative angular movement of at least one of the access ports to provide flexibility for positioning surgical instruments introduced through the at least one access port; wherein the flexible support includes at least one flexible bellow; wherein the rigid body includes a rigid top body and a rigid bellow support, wherein the rigid top body and the rigid bellow support compress an outer peripheral edge of the flexible support therebetween to form a sealing engagement between the rigid body and the flexible support.

2. The access device as recited in claim 1, wherein the at least one flexible bellow includes at least one of a rubber material a rubber-like material, and/or a VersaFlex material.

3. The access device as recited in claim 1, wherein the rigid bellow support includes at least one support rib extending proximally from the rigid bellow support into the bellow to inhibit inversion of the bellow during instrument insertion into one of the access ports.

4. The access device as recited in claim 1, wherein at least one of the access ports includes a compression ring engaged to a distal end of the access port with an inner edge of the flexible support compressed between the access port and the compression ring to form a sealing engagement between the access port and the flexible support.

5. The access device as recited in claim 4, wherein the at least one access port and compression ring include an axially opposed pair of gripping rims with a portion of the flexible support gripped between the gripping rims.

6. The access device as recited in claim 5, wherein the flexible support has a respective receptacle groove defined therein for engaging each of the gripping rims.

7. The access device as recited in claim 1, wherein at least one of the access ports connects to the rigid body through the flexible support, wherein the flexible support has a single bellow.

8. The access device as recited in claim 1, wherein the flexible support includes a bellow with a single sigmoidal cross-section that positions a distal end of the at least one access port within the multiport end cap.

9. The access device as recited in claim 1, wherein the flexible support includes a bellow with an accordion cross-section that spaces a distal end of the at least one access port proximally from the multiport end cap.

10. The access device as recited in claim 1, wherein the flexible support includes a bellow with a perimeter shape about the at least one access port that includes at least one of round and diamond shaped.

11. The access device as recited in claim 1, further comprising:
a bottom body having a distally extending tubular body with an access channel defined therethrough for accommodating surgical instruments from the access ports into the body of a patient.

12. The access devise as recited in claim 11, wherein the bottom body includes a gas inlet in fluid communication with the access channel.

13. The access device as recited in claim 12, wherein the access ports are configured to form a mechanical seal for insufflation gas for when instruments are inserted through the access ports and when no instruments are inserted through the access ports.

14. The access device as recited in claim 11, wherein the tubular body is configured for introduction through a body lumen or through a single incision formed in the wall of the abdominal cavity of a patient.

15. The access device as recited in claim 11, wherein the tubular body is configured for trans-anal introduction.

16. The access device as recited in claim 11, wherein the end cap is configured for complete 360° axial rotation relative to the bottom body.

17. The access device as recited in claim 11, wherein the tubular body is mounted to a main ring portion of the bottom body, and wherein the tubular body is of a less rigid material than that of the main ring portion.

18. The access device as recited in claim 11, wherein the rigid body includes at least one flexible tab configured to engage and disengage the bottom body to selectively permit or prevent relative axial rotation of the multiport end cap and bottom body.

19. The access device as recited in claim 1, wherein each of the access ports includes a respective seal configured to seal against gas flow when no surgical instrument is introduced therethrough, and to seal around surgical instruments introduced therethrough.

20. An access device for surgical procedures comprising:
a multiport end cap including a rigid body with a flexible support sealingly mounted to the rigid body with a plurality of separate access pots for accommodating introduction of individual surgical instruments into a body of a patient, at least one of the access ports sealingly attached to the flexible support and extending in a proximal direction therefrom, wherein the flexible support is of a material more flexible than those of the rigid body and access ports to provide for relative angular movement of at least one of the access ports to provide flexibility for positioning surgical instruments introduced through the at least one access port;

wherein there are three access ports extending proximally from the end cap;

wherein two of the access ports connect to the rigid body through the flexible support, wherein the flexible support has two bellows, one for each of the two access ports;

wherein the rigid support includes a respective support rib extending proximally from the rigid support into each one of the two bellows, respectively, to inhibit inversion of the two bellows during instrument insertion into the access port.

21. An access device for surgical procedures comprising:
a multiport end cap including a rigid body with a flexible support sealingly mounted to the rigid body with a plurality of separate access ports for accommodating introduction of individual surgical instruments into a body of a patient, at least one of the access ports sealingly attached to the flexible support and extending in a proximal direction therefrom, wherein the flexible support is of a material more flexible than those of the rigid body and access ports to provide for relative angular movement of at least one of the access ports to provide flexibility for positioning surgical instruments introduced through the at least one access port;

wherein there are three access ports extending proximally from the end cap;

wherein two of the access ports connect to the rigid body through the flexible support, wherein the flexible support has two bellows, one for each of the two access ports; and a second flexible support with a single bellow for connecting a third one of the three access ports to the rigid body.

22. An access device for surgical procedures comprising:
a multiport end cap including a rigid body with a flexible support sealingly mounted to the rigid body with a plurality of separate access ports for accommodating introduction of individual surgical instruments into a body of a patient, at least one of the access ports sealingly attached to the flexible support and extending in a proximal direction therefrom, wherein the flexible support is of a material more flexible than those of the rigid body and access ports to provide for relative angular movement of at least one of the access ports to provide flexibility for positioning surgical instruments introduced through the at least one access port;

wherein there are three access ports extending proximally from the end cap;

wherein the three access ports connect to the rigid body through the flexible support, wherein the flexible support has three bellows, one for each of the three access ports;

wherein the rigid support includes a respective support rib extending proximally from the rigid support into each one of two of the bellows, respectively, to inhibit inversion of the two bellows during instrument insertion into the access port.

\* \* \* \* \*